(12) United States Patent
Kageyama et al.

(10) Patent No.: US 12,089,808 B2
(45) Date of Patent: Sep. 17, 2024

(54) ENDOSCOPE BONDING STRUCTURE AND ENDOSCOPE

(71) Applicant: OLYMPUS CORPORATION, Tokyo (JP)

(72) Inventors: Naohiro Kageyama, Kodaira (JP); Takaharu Fujii, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 769 days.

(21) Appl. No.: 17/098,770

(22) Filed: Nov. 16, 2020

(65) Prior Publication Data

US 2021/0059505 A1 Mar. 4, 2021

Related U.S. Application Data

(63) Continuation of application No. PCT/JP2019/005079, filed on Feb. 13, 2019.

(30) Foreign Application Priority Data

Jun. 6, 2018 (JP) ................................. 2018-108492

(51) Int. Cl.
*A61B 1/00* (2006.01)
*G02B 23/24* (2006.01)

(52) U.S. Cl.
CPC .......... *A61B 1/0008* (2013.01); *A61B 1/0011* (2013.01); *G02B 23/2423* (2013.01)

(58) Field of Classification Search
CPC ............ G02B 23/2484; G02B 23/2423; G02B 23/243; G02B 23/2476; A61B 1/00096; A61B 1/0011; A61B 1/051; A61B 1/05; A61B 1/0008; A61B 1/00163
See application file for complete search history.

(56) References Cited

U.S. PATENT DOCUMENTS

| | | | |
|---|---|---|---|
| 2009/0122320 A1 | 5/2009 | Peterson et al. | |
| 2014/0128669 A1* | 5/2014 | Kobayashi | C08L 33/04 600/101 |
| 2015/0316742 A1 | 11/2015 | Jono et al. | |
| 2016/0353983 A1* | 12/2016 | Onoe | A61B 1/00096 |

(Continued)

FOREIGN PATENT DOCUMENTS

| | | |
|---|---|---|
| JP | 2001-133671 A | 5/2001 |
| JP | 2011-200397 A | 10/2011 |

(Continued)

OTHER PUBLICATIONS

International Search Report dated May 14, 2019 received in PCT/JP2019/005079.

*Primary Examiner* — Alexandra L Newton
(74) *Attorney, Agent, or Firm* — Scully, Scott, Murphy & Presser, P.C.

(57) ABSTRACT

An endoscope bonding structure includes a distal end rigid member, a tubular body, and a bonding agent. The distal end rigid member includes a first outer diameter part and a second outer diameter part. The tubular body includes a first inner diameter part and a second inner diameter part. An outer diameter of an outer periphery of the second outer diameter part decreases as a distance increases toward a proximal end side. The tubular body is fitted to an outer periphery in a state in which the tubular body is pressed to a distal end side.

19 Claims, 9 Drawing Sheets

(56) References Cited

U.S. PATENT DOCUMENTS

2017/0064164 A1\* 3/2017 Nishihara .......... A61B 1/00045
2017/0245734 A1\* 8/2017 Kaneko .................. A61B 1/307

FOREIGN PATENT DOCUMENTS

| WO | 2011/133187 A1 | 10/2011 | | |
|---|---|---|---|---|
| WO | 2014/088024 A1 | 6/2014 | | |
| WO | WO-2016181724 A1 \* | 11/2016 | .......... | A61B 1/0008 |

\* cited by examiner

ENDOSCOPE BONDING STRUCTURE AND ENDOSCOPE

CROSS REFERENCE TO RELATED APPLICATION

This application is a continuation application of PCT/JP2019/005079 filed on Feb. 13, 2019 and claims benefit of Japanese Application No. 2018-108492 filed in Japan on Jun. 6, 2018, the entire contents of which are incorporated herein by this reference.

BACKGROUND OF THE INVENTION

1. Field of the Invention

The present invention relates to an endoscope bonding structure and an endoscope in each of which a tubular body is bonded and fitted to an outer periphery of a shaft.

2. Description of the Related Art

Recently, endoscopes have been widely used in a medical field and an industrial field. With an endoscope used in the medical field, an organ in a body cavity as a subject can be observed through an elongated insertion portion inserted into the body cavity, and various kinds of treatment can be performed as necessary by using a treatment instrument inserted into a treatment instrument insertion channel included in the endoscope.

With an endoscope used in the industrial field, observation and examination involving various treatments can be performed on flaw, corrosion, and the like of a site to be examined in an object such as a jet engine or a pipe at a factory through an elongated insertion portion of the endoscope inserted into the object.

Known endoscopes include what is called a flexible endoscope including a flexible insertion portion and what is called a rigid endoscope including a rigid insertion portion.

In a known configuration of the insertion portion of the rigid endoscope, a distal end rigid member that is a shaft is bonded and fixed to a distal end of a tubular body in a longitudinal direction.

For example, a distal end of a known light guide in the longitudinal direction, or a distal end of a relay lens provided in an image pickup unit or insertion portion including an objective lens unit in the longitudinal direction is fixed to the distal end rigid member.

Specifically, the distal end rigid member is configured by a fitting site that is fitted into the tubular body through a distal end opening of the tubular body in the longitudinal direction, and a blockage member that blocks the distal end opening of the tubular body.

The distal end rigid member is bonded and fixed to the tubular body by a bonding agent filling a gap between an outer periphery of the fitting site and an inner periphery of the tubular body and a bonding agent filling a gap between a distal end of the tubular body in the longitudinal direction and a site of the blockage member opposing to the distal end of the tubular body in the longitudinal direction.

In the bonding and fixation of the distal end rigid member to the tubular body, a method is employed in which the distal end side of the tubular body in the longitudinal direction is fitted to the outer periphery of the fitting site in a state in which a bonding agent is applied to the outer periphery of the fitting site.

Japanese Patent Application Laid-Open Publication No. 2011-200397 discloses a configuration in which a stepped part is provided to the outer periphery of the fitting site of the distal end rigid member to have a diameter that decreases in a stepwise manner as a distance increases toward a back side in the longitudinal direction, and a circumferential step for pressing a bonding agent is provided to the inner periphery of the tubular body on the distal end side in the longitudinal direction.

SUMMARY OF THE INVENTION

An endoscope bonding structure according to an aspect of the present invention is an endoscope bonding structure including: a shaft extending in a longitudinal direction; a tubular body fitted to an outer periphery of the shaft in the longitudinal direction in a loosely-fitted state; and a bonding agent filling a gap between the outer periphery of the shaft and an inner periphery of the tubular body. The shaft includes a first outer diameter part formed at a first position on the outer periphery, and a second outer diameter part that is formed at a second position on the outer periphery, is smaller than the first outer diameter part, and has a first length in the longitudinal direction. The tubular body includes a first inner diameter part formed on one side of the inner periphery of the tubular body in the longitudinal direction, the first inner diameter part having a diameter larger than a diameter of the first outer diameter part, the first inner diameter part having a second length equal to or longer than the first length in the longitudinal direction, and a second inner diameter part formed continuously with the first inner diameter part on another side of the inner periphery of the tubular body in the longitudinal direction, the second inner diameter having a diameter smaller than the diameter of the first inner diameter part. The second outer diameter part is formed so that an outer diameter of the outer periphery decreases as a distance increases in a direction opposite to the first outer diameter part. The tubular body is fitted to the outer periphery of the shaft in a state in which the tubular body is pressed to the one side so that the first inner diameter part side moves toward the first position through the second position.

An endoscope according to another aspect of the present invention is an endoscope including: a distal end member extending in a longitudinal direction; a tubular body fitted to an outer periphery of the distal end member in the longitudinal direction in a loosely-fitted state; and a bonding agent filling a gap between the outer periphery of the distal end member and an inner periphery of the tubular body. The distal end member includes a first outer diameter part formed at a first position on the outer periphery, and a second outer diameter part that is formed at a second position on the outer periphery, is smaller than the first outer diameter part, and has a first length in the longitudinal direction. The tubular body includes a first inner diameter part formed on a distal end side of the inner periphery of the tubular body in the longitudinal direction, the first inner diameter part having a diameter larger than a diameter of the first outer diameter part, the first inner diameter part having a second length equal to or longer than the first length in the longitudinal direction, and a second inner diameter part formed continuously with the first inner diameter part on a proximal end side of the inner periphery of the tubular body in the longitudinal direction, the second inner diameter having a diameter smaller than the diameter of the first inner diameter part. The second outer diameter part is formed so that an outer diameter of the outer periphery decreases as a distance increases in a direction opposite to the first outer diameter part. The tubular body is fitted to the outer periphery of the distal end member in a state in which the tubular body is pressed to the distal end side so that the first inner diameter part side moves toward the first position through the second position.

DETAILED DESCRIPTION OF THE PREFERRED EMBODIMENTS

Embodiments of the present invention will be described below with reference to the accompanying drawings. Note that the drawings are schematic, for example, relations among thicknesses and widths of members and ratios of the thicknesses of the members are different from the relations and ratios in reality, and the drawings include parts, relations and ratios of dimensions of which are different among the drawings.

First Embodiment

Figure 1:
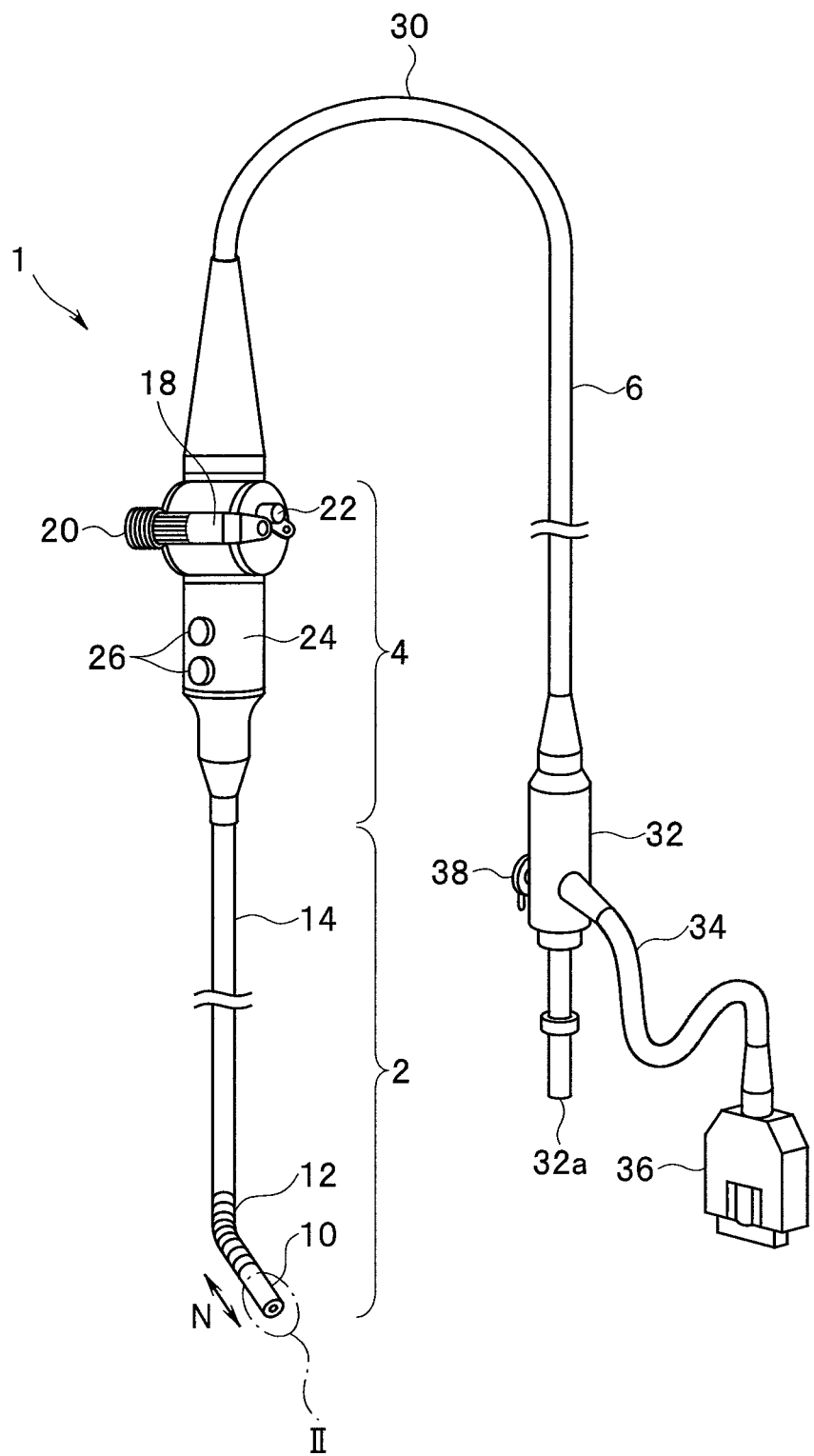
FIG. 1 is a perspective view schematically illustrating a configuration of an endoscope including a bonding structure of a first embodiment.

FIG. 1 is a perspective view schematically illustrating a configuration of an endoscope having a bonding structure of the present embodiment.

As illustrated in FIG. 1, the endoscope 1 is configured by including, as main parts, an insertion portion 2 that is elongated and inserted into a subject, an operation portion 4, a universal cable 30, and a connector 32.

The insertion portion 2 is configured by including, as main parts sequentially from a distal end side in a longitudinal direction N, a distal end portion 10, a bending portion 12 that is freely bendable in a plurality of directions, and a pipe portion 14 that is elongated in the longitudinal direction N of the insertion portion 2 and rigid. Accordingly, the endoscope 1 in the present embodiment is configured as a rigid endoscope including the insertion portion 2 that is hard.

The operation portion 4 is provided continuously with a proximal end of the pipe portion 14 in the longitudinal direction N. The operation portion 4 is provided with an operation lever 18 that is freely rotatable and performs a bending operation of the bending portion 12 in an up-down direction, and an operation lever 20 that is freely rotatable and performs a bending operation of the bending portion 12 in a right-left direction.

The operation portion 4 is also provided with a fixation lever 22 that fixes a rotational position of the operation lever 18. Note that although not illustrated, the operation portion 4 is also provided with another fixation lever that fixes a rotational position of the operation lever 20.

In addition, the operation portion 4 includes a grip 24 that is grasped by an operator, and the grip 24 is provided with a remote switch 26. The remote switch 26 remotely operates various instruments connected with the connector 32.

The universal cable 30 is extended from the operation portion 4 and provided with the connector 32 at an extension end.

A connection end part 32a of a nonillustrated light guide is provided as an extension to the connector 32. A camera cable 34 is extended from the connector 32.

A camera connector 36 is provided at an extension end of the camera cable 34. The camera connector 36 is connected with a nonillustrated camera control unit that performs signal processing of an optical image of inside of the subject, which is picked up by a nonillustrated image pickup unit. Note that the camera control unit is connected with a monitor that performs image display of an optical image, a video recording device, or the like, which are all not illustrated.

In addition, a ventilation pipe sleeve 38 is provided to the connector 32. The endoscope 1 normally has a watertight structure, but when the ventilation pipe sleeve 38 is opened, inside of the endoscope 1 communicates with outside. Thus, with the ventilation pipe sleeve 38, it is possible to select a state of communication between the inside and outside of the endoscope 1 and to examine water leakage of the endoscope 1.

Figure 2:
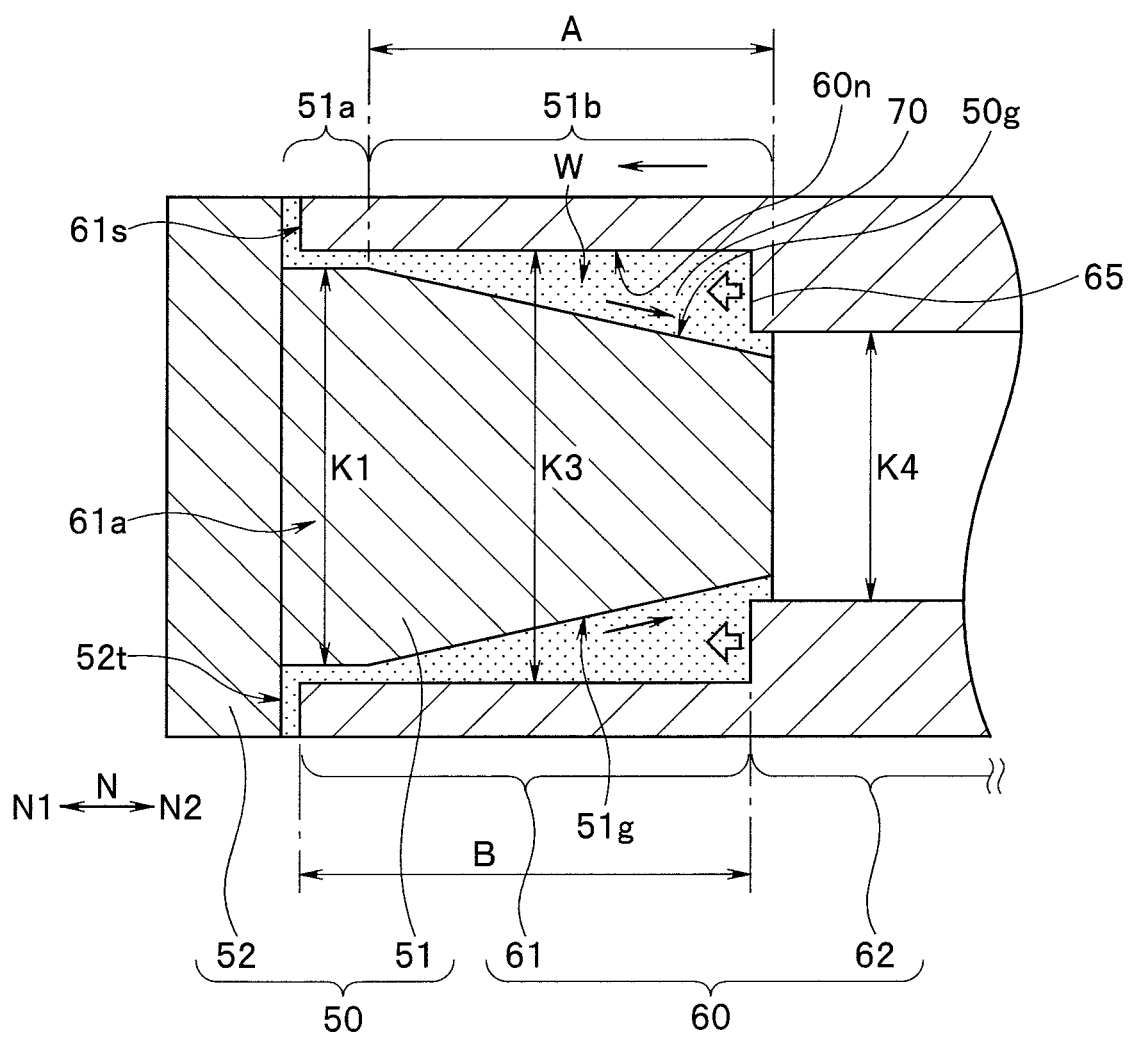
FIG. 2 is a partial cross-sectional view schematically illustrating a bonding structure of a site surrounded by line II at a distal end portion in FIG. 1.

Subsequently, a bonding structure of the distal end portion in FIG. 1 will be described with reference to FIGS. 2 and 3. FIG. 2 is a partial cross-sectional view schematically illustrating a bonding structure of a site surrounded by line II at the distal end portion in FIG. 1, and FIG. 3 is a partial cross-sectional view illustrating a halfway process in which a tubular body is fitted to an outer periphery of a fitting portion of a distal end rigid member in FIG. 2 in an assembly process.

Figure 3:
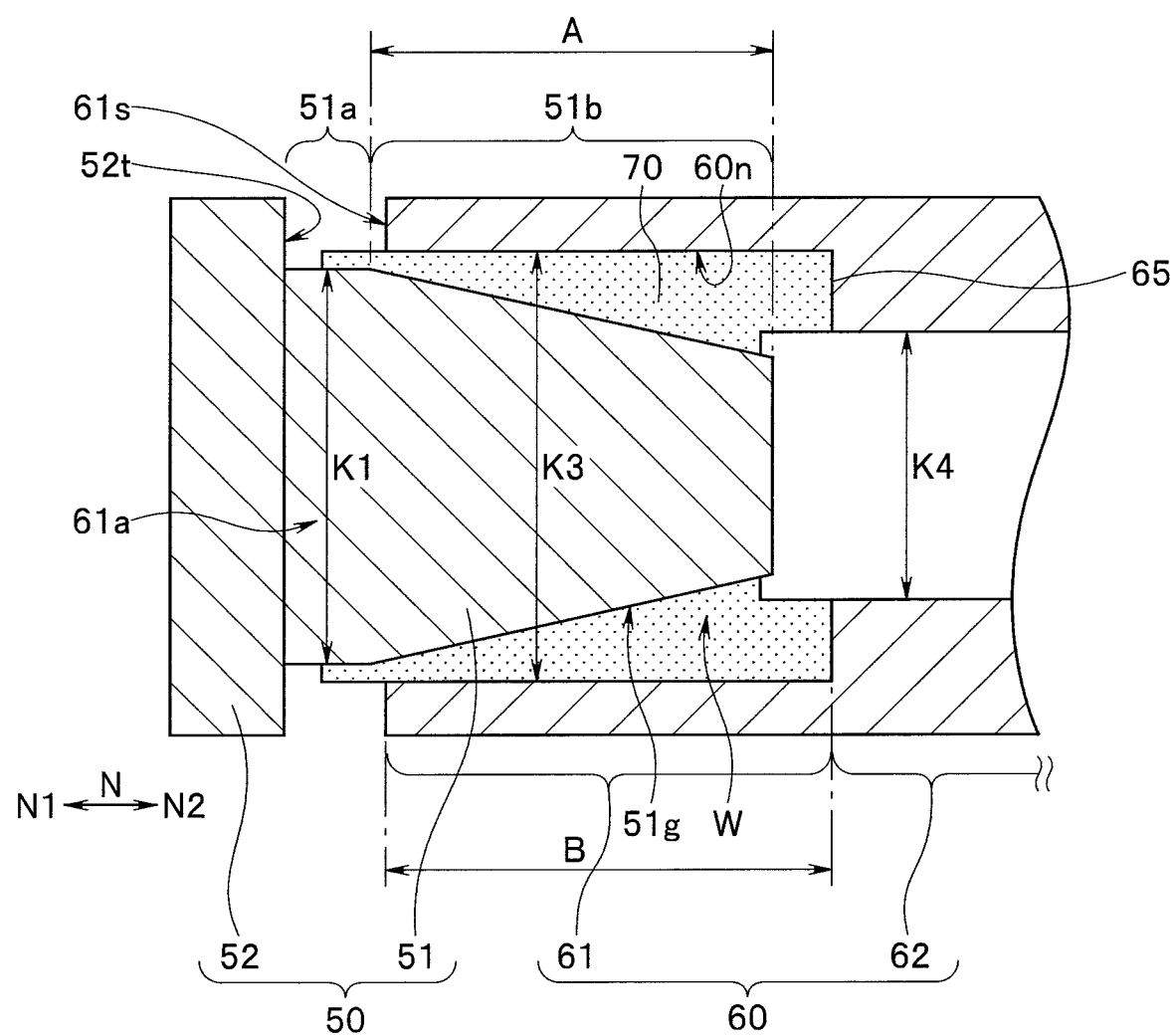
FIG. 3 is a partial cross-sectional view illustrating a halfway process in which a tubular body is fitted to an outer periphery of a fitting portion of a distal end rigid member in FIG. 2 in an assembly process.

As illustrated in FIGS. 2 and 3, the distal end portion 10 is configured such that a tubular body 60 that configures an exterior of the distal end portion 10 is bonded and fixed to a distal end rigid member 50 that is a shaft.

Note that a distal end of the light guide in the longitudinal direction N, which is inserted into the insertion portion 2, the operation portion 4, the universal cable 30, and the connector 32, which are not illustrated, a nonillustrated image pickup unit including an objective lens unit provided in the distal end portion 10, and the like are fixed to the distal end rigid member 50.

The distal end rigid member 50 and the tubular body 60 may be each made of metal or may be each made of resin that can be subjected to known autoclave sterilization processing.

The distal end rigid member 50 is configured by including a fitting portion 51 and a blockage member 52 as main parts.

The fitting portion 51 includes a first outer diameter part 51$a$ formed at a first position on an outer periphery 51$g$ and having an outer diameter K1, and a second outer diameter part 51$b$ that is formed at a second position on the outer periphery 51$g$ and is smaller than the first outer diameter part 51$a$.

Note that the first position and the second position on the outer periphery 51$g$ are provided in a longitudinal direction N of the distal end rigid member 50, which is aligned with the longitudinal direction N of the insertion portion 2, and the first position is positioned on a distal end side N1 that is one side of the second position in the longitudinal direction N.

The second outer diameter part 51$b$ has a first length A in the longitudinal direction N. The second outer diameter part 51$b$ is formed to have a diameter smaller than the diameter of the first outer diameter part 51$a$.

Specifically, the second outer diameter part 51$b$ is formed so that an outer diameter of the outer periphery 51$g$ decreases gradually as a distance increases toward a proximal end side N2 that is the other side opposite to the first outer diameter part 51$a$ in the longitudinal direction N. In other words, the outer periphery 51$g$ of the second outer diameter part 51$b$ is formed as a tilted surface of a diameter that decreases gradually as a distance increases toward the proximal end side N2 in the longitudinal direction N.

A distal end of the first outer diameter part 51$a$ of the fitting portion 51 in the longitudinal direction N is provided with the blockage member 52 that blocks an opening 61$a$ of a first inner diameter part 61 of the tubular body 60 on the distal end side N1, which will be described later, when the tubular body 60 is fitted to the outer periphery 51$g$ of the distal end rigid member 50.

Note that the blockage member 52 has a diameter that is larger than the diameter of the first outer diameter part 51$a$ and substantially equal to a diameter of the tubular body 60.

The tubular body 60 is fitted to the outer periphery 51$g$ of the fitting portion 51 of the distal end rigid member 50 in the longitudinal direction N in a loosely-fitted state, and includes the first inner diameter part 61 and a second inner diameter part 62.

The first inner diameter part 61 is formed on the distal end side N1 of an inner periphery 60$n$ of the tubular body 60, has a diameter larger than the diameter of the first outer diameter part 51$a$ (K3>K1), and has a second length B equal to or longer than the first length A (B≥A) in the longitudinal direction N. Note that the second length B is set to be equal to or shorter than a length of the fitting portion 51.

The second inner diameter part 62 is formed continuously with the first inner diameter part 61 on the proximal end side N2 of the inner periphery 60$n$ of the tubular body 60 and has a diameter smaller than the diameter of the first inner diameter part 61 (K4<K3).

Accordingly, since the second inner diameter part 62 is formed to have a diameter smaller than the diameter of the first inner diameter part 61, a step 65 is circumferentially formed between the first inner diameter part 61 and the second inner diameter part 62 in the longitudinal direction N on the inner periphery 60$n$ of the tubular body 60.

A bonding agent 70 fills a gap between the outer periphery 51$g$ of the fitting portion 51 of the distal end rigid member 50 and the inner periphery 60$n$ of the tubular body 60. The tubular body 60 is bonded and fixed to the outer periphery 51$g$ by the bonding agent 70.

Specifically, in a state in which the first outer diameter part 51$a$ and the second outer diameter part 51$b$ are covered by the first inner diameter part 61 as illustrated in FIG. 2, the tubular body 60 is bonded and fixed to the outer periphery 51$g$ by the bonding agent 70 filling a gap between the outer periphery 51$g$ and an inner periphery of the first inner diameter part 61 and a gap between a surface 52$t$ of the blockage member 52 on the proximal end side N2 in the longitudinal direction N and a distal end surface 61$s$ of the first inner diameter part 61 on the distal end side N1 in the longitudinal direction N.

Note that, at fitting to the outer periphery 51$g$ of the fitting portion 51, the tubular body 60 is fitted to the outer periphery 51$g$ of the fitting portion 51 as the tubular body 60 is pressed to the distal end side N1 in the longitudinal direction N so that the first inner diameter part 61 side, in other words, the opening 61$a$ side moves toward the first position through the second position on the outer periphery 51$g$ in a state in which the bonding agent 70 is circumferentially and uniformly applied to the outer periphery 51$g$.

In the pressing, the bonding agent 70 applied to the outer periphery 51$g$ is pressed to the distal end side N1 in a state in which pressing pressure toward the distal end side N1 is increased by the step 65.

As described above, the second outer diameter part 51$b$ of the outer periphery 51$g$ is formed to have an outer diameter that decreases gradually as a distance increases toward the proximal end side N2.

In addition, the first inner diameter part 61 has the second length B equal to or longer than the first length A of the second outer diameter part 51$b$ (B≥A) in the longitudinal direction N and is set to be equal to or shorter than the length of the fitting portion 51.

Accordingly, a large space W is formed between the first inner diameter part 61 and the second outer diameter part 51$b$ in the longitudinal direction N, and thus at pressing, the bonding agent 70 stays in a gap between the surface 52$t$ of the blockage member 52 and the distal end surface 61$s$ of the first inner diameter part 61 but hardly leaks to outside from the gap, and then flows to the proximal end side N2 along the outer periphery 51$g$ in the space W. As a result, the bonding agent 70 uniformly remains on the outer periphery 51$g$.

In this manner, it is possible to provide the bonding structure of the endoscope 1, and the endoscope 1, each having a configuration in which the bonding agent 70 uniformly remains on the outer periphery 51$g$ without leakage in a state in which the tubular body 60 is fitted to the outer periphery 51$g$ of the fitting portion 51 of the distal end rigid member 50.

Figure 4:
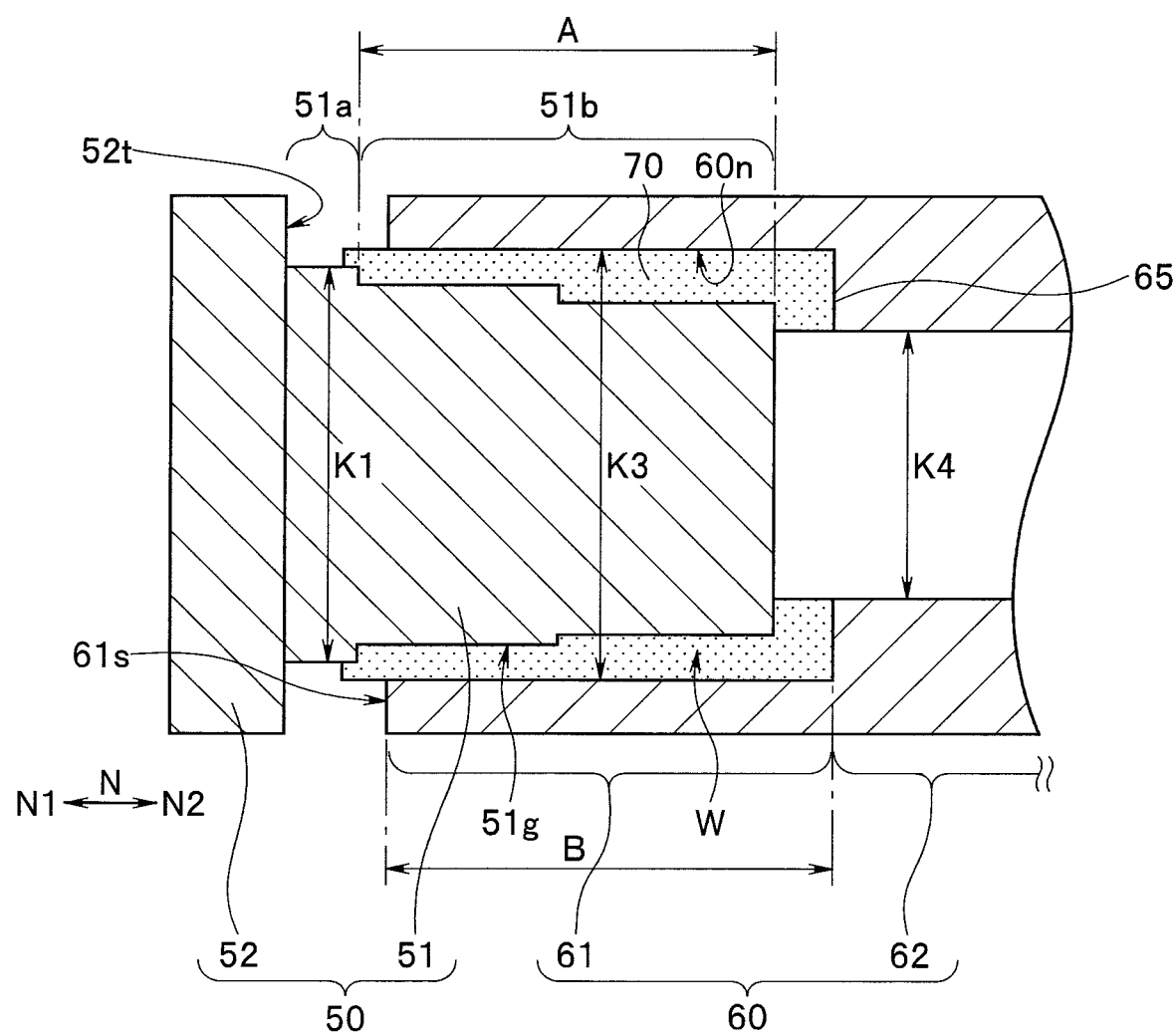
FIG. 4 is a partial cross-sectional view illustrating a modification of an outer peripheral shape of the fitting portion of the distal end rigid member in FIG. 2.

Note that a modification will be illustrated with reference to FIG. 4. FIG. 4 is a partial cross-sectional view illustrating a modification of an outer peripheral shape of the fitting portion of the distal end rigid member in FIG. 2.

In the present embodiment described above, the second outer diameter part 51$b$ is formed so that the outer diameter of the outer periphery 51$g$ decreases gradually as a distance increases toward the proximal end side N2. Specifically, it is described that the outer periphery 51$g$ of the second outer diameter part 51$b$ is formed as a tilted surface of a diameter that decreases gradually as a distance increases toward the proximal end side N2.

The present embodiment is not limited to this configuration, but it is possible to obtain effects same as effects of the present embodiment described above even when the second outer diameter part 51$b$ is formed so that the outer diameter of the outer periphery 51g decreases in a stepwise manner as a distance increases toward the proximal end side N2 as illustrated in FIG. 4.

Second Embodiment

Figure 5:
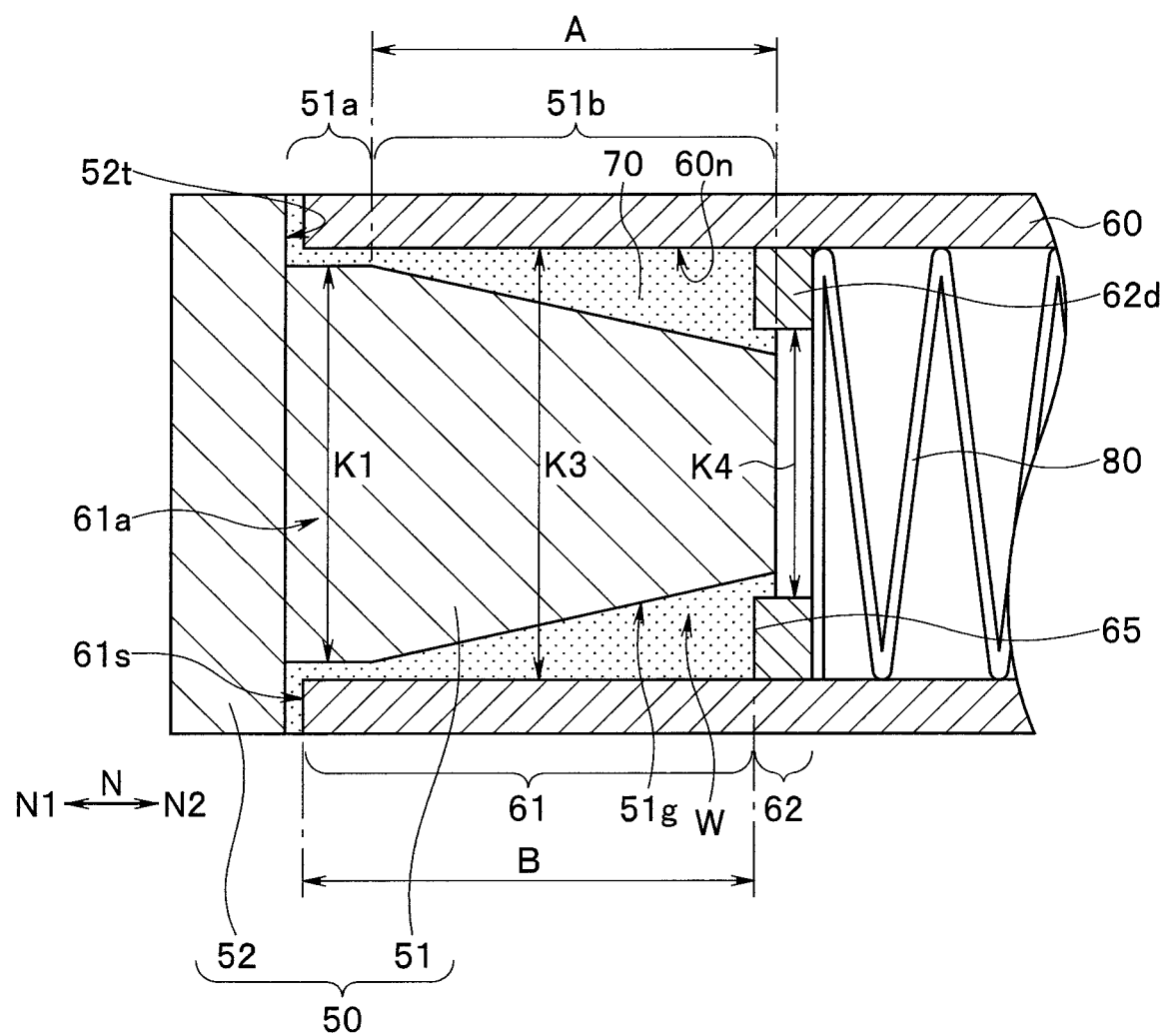
FIG. 5 is a partial cross-sectional view schematically illustrating an endoscope bonding structure of a second embodiment.

FIG. 5 is a partial cross-sectional view schematically illustrating an endoscope bonding structure of the present embodiment.

An endoscope bonding structure and an endoscope of the second embodiment are different from the above-described endoscope bonding structure of the first embodiment illustrated in FIGS. 1 to 3 in that the second inner diameter part of the tubular body is configured as a ring that is freely movable in the longitudinal direction, and the ring is pressed to the distal end side in the longitudinal direction by an urging member.

Thus, only this difference will be described below, components which are the same as components of the first embodiment will be denoted by the same reference signs, and description of such components will be omitted.

As illustrated in FIG. 5, in the present embodiment, the second inner diameter part 62 is configured as a ring 62d that is freely movable on the inner periphery 60n of the tubular body 60 in the longitudinal direction N.

The ring 62d is pressed to the distal end side N1 by a compression spring (hereinafter simply referred to as a spring) 80 that is an urging member.

Note that the spring 80 is fixed to the inner periphery 60n on the proximal end side N2 and fixed to the ring 62d on the distal end side N1. A strength of pressing to the distal end side N1 by the ring 62d can be freely set by changing a strength of the spring 80.

Note that the other configuration is same as the configuration of the first embodiment described above.

With such a configuration, the step 65 formed by the ring 62d reliably presses the bonding agent 70 applied to the outer periphery 51g to the distal end side N1 through urging by the spring 80.

Thus, even when a bonding agent having a higher viscosity is used as the bonding agent 70, the bonding agent can be more reliably pressed and stretched to the distal end side N1 than in the first embodiment described above.

Accordingly, the bonding agent 70 having a high viscosity can be caused to uniformly remain on the outer periphery 51g without leakage. Note that the other effects are same as the effects of the first embodiment described above.

Third Embodiment

Figure 6:
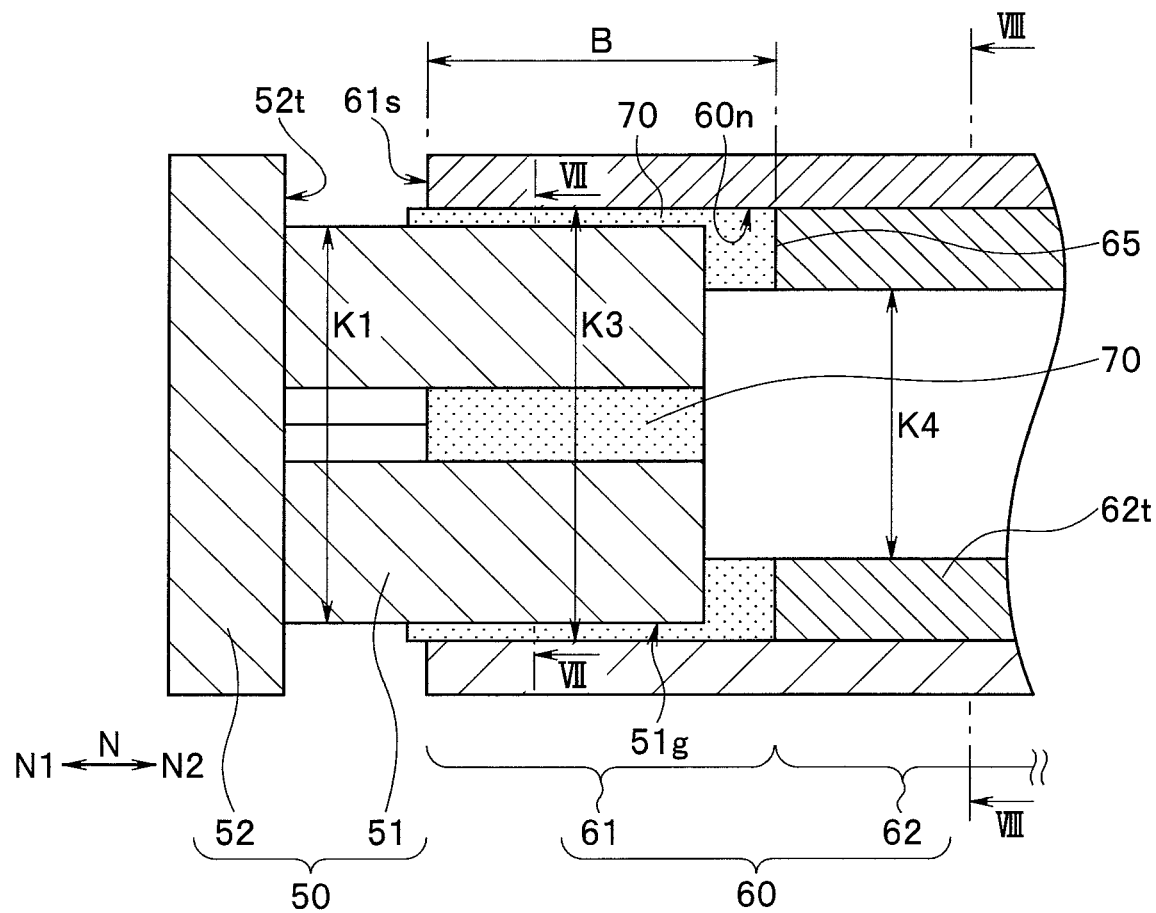
FIG. 6 is a partial cross-sectional view schematically illustrating an endoscope bonding structure of a third embodiment.
Figure 7:
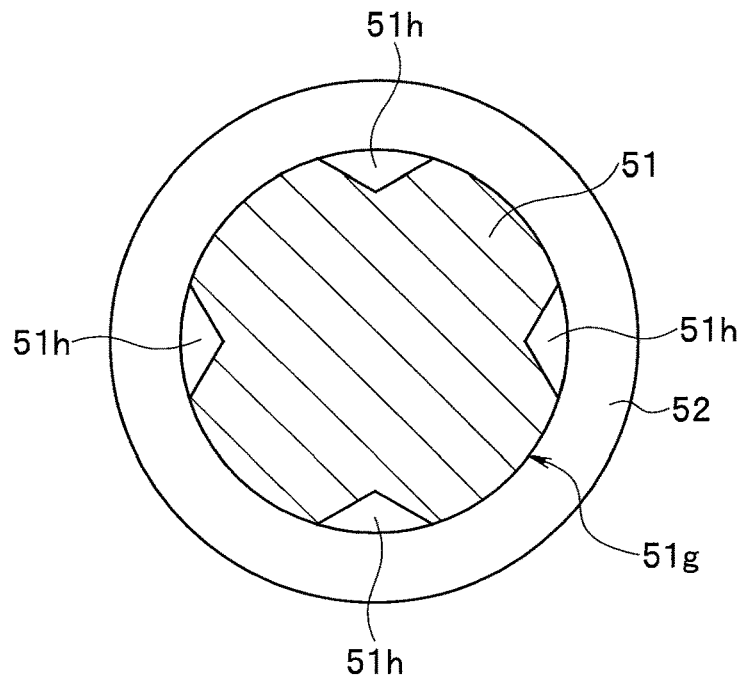
FIG. 7 is a cross-sectional view of the distal end rigid member taken along line in FIG. 6.
Figure 8:
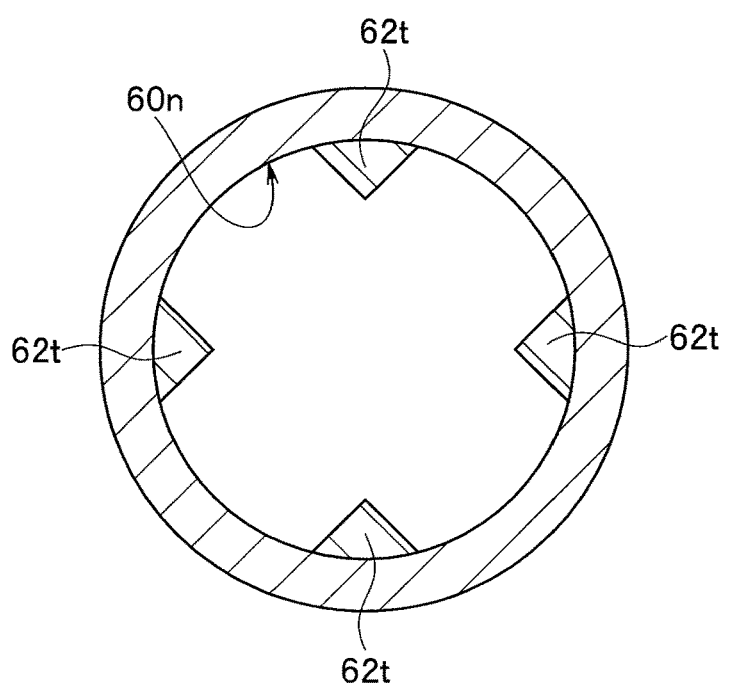
FIG. 8 is a cross-sectional view of the tubular body taken along line VIII-VIII in FIG. 6.

FIG. 6 is a partial cross-sectional view schematically illustrating an endoscope bonding structure of the present embodiment, FIG. 7 is a cross-sectional view of the distal end rigid member taken along line VII-VII in FIG. 6, and FIG. 8 is a cross-sectional view of the tubular body taken along line VIII-VIII in FIG. 6.

An endoscope bonding structure and an endoscope of the third embodiment are different from the above-described endoscope bonding structure of the first embodiment illustrated in FIGS. 1 to 3 in that a groove to which protrusions provided on the inner periphery of the tubular body is fitted are formed in the longitudinal direction at the outer periphery of the fitting portion of the distal end rigid member.

Thus, only this difference will be described below, components which are the same as components of the first embodiment will be denoted by the same reference signs, and description of such components will be omitted.

As illustrated in FIG. 6, the distal end portion 10 is configured such that the tubular body 60 that configures the exterior of the distal end portion 10 is bonded and fixed to the distal end rigid member 50 that is the shaft.

Note that the distal end of the light guide in the longitudinal direction N, which is inserted into the insertion portion 2, the operation portion 4, the universal cable 30, and the connector 32, which are not illustrated, the nonillustrated image pickup unit including the objective lens unit provided in the distal end portion 10, and the like are fixed to the distal end rigid member 50.

The distal end rigid member 50 and the tubular body 60 may be made of metal or may be made of resin that can be subjected to known autoclave sterilization processing.

The distal end rigid member 50 is configured by including the fitting portion 51 and the blockage member 52 as main parts.

The fitting portion 51 is formed to have a predetermined length in the longitudinal direction N so that the outer periphery 51g has a constant diameter.

A groove 51h is formed at the outer periphery 51g of the fitting portion 51, for example, at every 90° in the longitudinal direction N.

The bonding agent 70 applied to the outer periphery 51g is fitted to each groove 51h, and in addition, a protrusion 62t to be described later is fitted to the groove 51h when the tubular body 60 is fitted to the outer periphery 51g of the fitting portion 51.

Note that a section of each groove 51h has, for example, a triangular shape in FIG. 7, but may have any other sectional shape. Moreover, the number of grooves 51h is not limited to four.

A distal end of the fitting portion 51 in the longitudinal direction N is provided with the blockage member 52 that blocks the opening 61a of the first inner diameter part 61 of the tubular body 60 on the distal end side N1, which will be described later, when the tubular body 60 is fitted to the outer periphery 51g of the fitting portion 51. Note that the blockage member 52 has a diameter larger than a diameter of the fitting portion 51 and substantially equal to the diameter of the tubular body 60.

The tubular body 60 is fitted to the outer periphery 51g of the fitting portion 51 of the distal end rigid member 50 in the longitudinal direction N in the loosely-fitted state, and includes the first inner diameter part 61 and the second inner diameter part 62.

The first inner diameter part 61 is formed on the distal end side N1 of the inner periphery 60n of the tubular body 60 and has a diameter larger than the diameter of the fitting portion (K3>K1).

As illustrated in FIG. 8, the second inner diameter part 62 is formed continuously with the first inner diameter part 61 on the proximal end side N2 of the inner periphery 60n of the tubular body 60, has a diameter smaller than the diameter of the first inner diameter part 61 (K4<K3), and is configured of the protrusion 62t formed on the inner periphery 60n, for example, at every 45° in the longitudinal direction N.

Each protrusion 62t is fitted to the corresponding groove 51h when the tubular body 60 is fitted to the outer periphery 51g of the fitting portion 51.

Note that the section of each protrusion 62t has, for example, a triangular shape in FIG. 8, but may have any other sectional shape. Moreover, the number of protrusions 62t is not limited to four.

Accordingly, the step 65 is formed for each protrusion 62t on the inner periphery 60n of the tubular body 60 since the second inner diameter part 62 is formed between the first inner diameter part 61 and the second inner diameter part 62 in the longitudinal direction N to have a diameter smaller than the diameter of the first inner diameter part 61.

The bonding agent 70 fills the gap between the outer periphery 51g of the fitting portion 51 of the distal end rigid member 50 and the inner periphery 60n of the tubular body 60. The tubular body 60 is bonded and fixed to the outer periphery 51g by the bonding agent 70.

Specifically, in a state in which the fitting portion 51 is covered by the first inner diameter part 61 as illustrated in FIG. 6, the tubular body 60 is bonded and fixed to the outer periphery 51g by the bonding agent 70 filling the gap between the outer periphery 51g and the inner periphery of the first inner diameter part 61 and the gap between the surface 52t of the blockage member 52 on the proximal end side N2 in the longitudinal direction N and the distal end surface 61s of the first inner diameter part 61 on the distal end side N1 in the longitudinal direction N.

Note that, at fitting to the outer periphery 51g of the fitting portion 51 of the distal end rigid member 50, the tubular body 60 is fitted to the outer periphery 51g of the distal end rigid member 50 as the first inner diameter part 61 side, in other words, the opening 61a side is pressed to the distal end side N1 in the longitudinal direction N in a state in which the bonding agent 70 is applied to each groove 51h.

In the pressing, the bonding agent 70 applied to each groove 51h is pressed to the distal end side N1 in a state in which the pressing pressure is increased by the step 65.

Along with the pressing, the bonding agent 70 in each groove 51h is pressed in a direction toward the outer periphery 51g of the fitting portion 51.

Accordingly, at pressing of the tubular body 60, the bonding agent 70 stays in the gap between the surface 52t of the blockage member 52 and the distal end surface 61s of the first inner diameter part 61 but hardly leaks to the outside from the gap, and then flows in the direction toward the outer periphery 51g. As a result, the bonding agent 70 uniformly remains on the outer periphery 51g.

In this manner, it is possible to provide the bonding structure of the endoscope 1 having a configuration in which the bonding agent 70 uniformly remains on the outer periphery 51g without leakage in a state in which the tubular body 60 is fitted to the outer periphery 51g of the fitting portion 51 of the distal end rigid member 50.

Note that the above-described second embodiment is also applicable to the present embodiment. Specifically, each protrusion 62t that is freely movable on the inner periphery 60n in the longitudinal direction N may be pressed to the distal end side N1 by using a spring.

Fourth Embodiment

Figure 9:
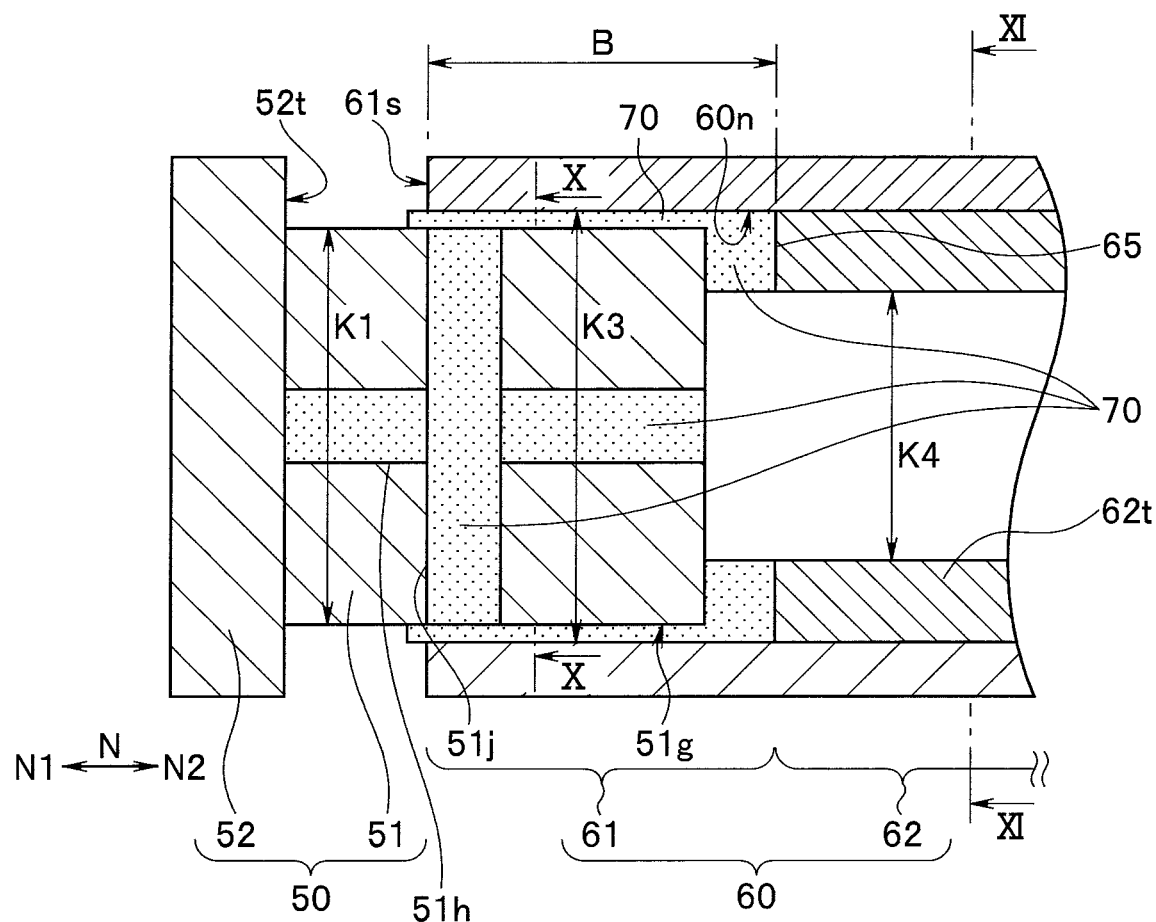
FIG. 9 is a partial cross-sectional view schematically illustrating an endoscope bonding structure of a fourth embodiment.
Figure 10:
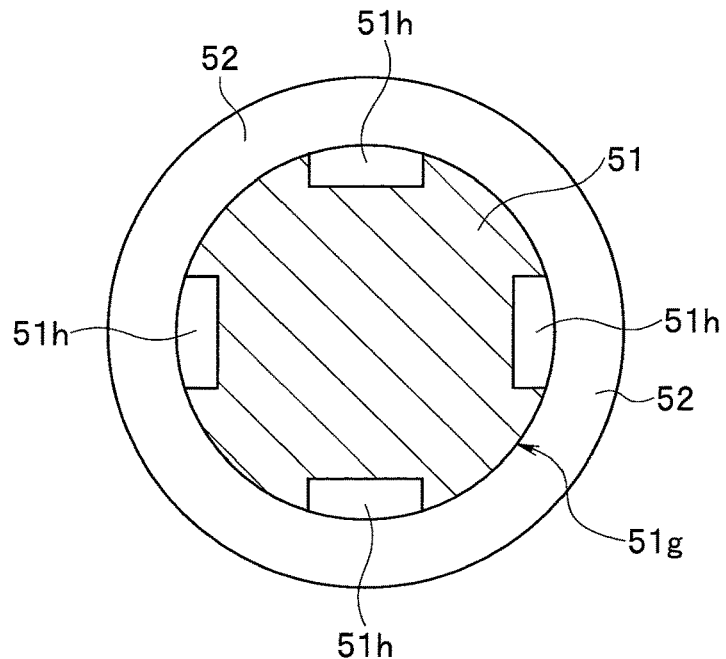
FIG. 10 is a cross-sectional view of the distal end rigid member taken along line X-X in FIG. 9.
Figure 11:
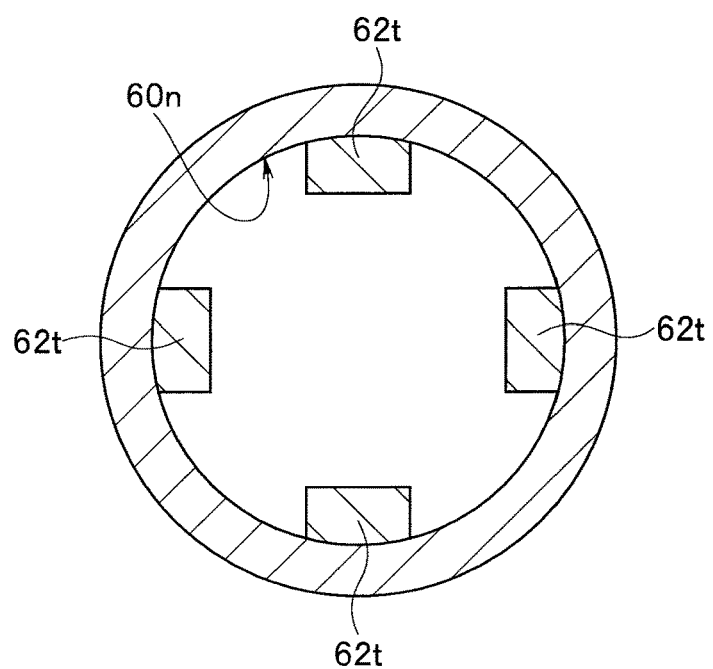
FIG. 11 is a cross-sectional view of the tubular body taken along line XI-XI in FIG. 9.

FIG. 9 is a partial cross-sectional view schematically illustrating an endoscope bonding structure of the present embodiment, FIG. 10 is a cross-sectional view of the distal end rigid member taken along line X-X in FIG. 9, and FIG. 11 is a cross-sectional view of the tubular body taken along line XI-XI in FIG. 9.

An endoscope bonding structure and an endoscope of the fourth embodiment are different from the above-described endoscope bonding structure of the third embodiment illustrated in FIGS. 6 to 8 in that grooves to which protrusions provided on the inner periphery of the tubular body are fitted are formed in an outer peripheral direction in addition to the longitudinal direction at the outer periphery of the fitting portion of the distal end rigid member.

Thus, only this difference will be described below, components which are the same as components of the third embodiment will be denoted by the same reference signs, and description of such components will be omitted.

As illustrated in FIG. 9, the groove 51h is formed at the outer periphery 51g of the fitting portion 51, for example, at every 90° in the longitudinal direction N, and a circumferential groove 51j is formed in a direction along the outer periphery 51g to connect the grooves 51h in the direction along the outer periphery 51g.

Note that the section of each groove 51h has, for example, a rectangular shape in FIG. 10, but may be any other sectional shape. Moreover, the number of grooves 51h is not limited to four.

As illustrated in FIG. 11, the second inner diameter part 62 includes the protrusion 62t formed in the longitudinal direction N, for example, at every 90° at the inner periphery 60n.

Each protrusion 62t is fitted to the corresponding groove 51h when the tubular body 60 is fitted to the outer periphery 51g of the fitting portion 51.

Note that the section of each protrusion 62t has, for example, a rectangular shape in FIG. 11, but may be any other sectional shape. Moreover, the number of protrusions 62t is not limited to four.

The bonding agent 70 fills the gap between the outer periphery 51g of the fitting portion 51 of the distal end rigid member 50 and the inner periphery 60n of the tubular body 60. The tubular body 60 is bonded and fixed to the outer periphery 51g by the bonding agent 70.

Specifically, the tubular body 60 is bonded and fixed to the outer periphery 51g by the bonding agent 70 filling the gap between the outer periphery 51g and the inner periphery of the first inner diameter part 61 and the gap between the surface 52t of the blockage member 52 on the proximal end side N2 in the longitudinal direction N and the distal end surface 61s of the first inner diameter part 61 on the distal end side N1 in a state in which the fitting portion 51 is covered by the first inner diameter part 61 as illustrated in FIG. 9.

Note that, at fitting to the outer periphery 51g of the fitting portion 51 of the distal end rigid member 50, the tubular body 60 is fitted to the outer periphery 51g of the distal end rigid member 50 as the first inner diameter part 61 side, in other words, the opening 61a side is pressed to the distal end side N1 in the longitudinal direction N in a state in which the bonding agent 70 is applied to each groove 51h.

In the pressing, the bonding agent 70 applied to each groove 51h is pressed to the distal end side N1 in a state in which the pressing pressure is increased by the step 65.

Along with the pressing, the bonding agent 70 in each groove 51h is pressed in the direction toward the outer periphery 51g of the fitting portion 51.

Accordingly, at pressing of the tubular body 60, the bonding agent 70 stays in the gap between the surface 52t of the blockage member 52 and the distal end surface 61s of the first inner diameter part 61 but hardly leaks to the outside from the gap, and then flows in the direction toward the outer periphery 51g while filling the circumferential groove 51j.

Accordingly, the bonding agent 70 is more likely to flow in the direction along the outer periphery 51g than in the third embodiment, and as a result, the bonding agent 70 is more likely to uniformly remain on the outer periphery 51g.

Note that the other effects are same as the effects of the third embodiment described above.

The above-described second embodiment is also applicable to the present embodiment. Specifically, each protrusion 62*t* that is freely movable on the inner periphery 60*n* in the longitudinal direction N may be pressed to the distal end side N1 by using a spring.

Moreover, the present invention is not limited to the above-described embodiments but may be modified as appropriate without departing from the gist or idea of the invention, which can be understood from the claims, the entire specification, and the drawings.

What is claimed is:

1. An endoscope bonding structure comprising:
    a shaft extending in a longitudinal direction, wherein the shaft comprises:
        a first part having a first outer diameter, and
        a second part having a distal portion having a second outer diameter smaller than the first outer diameter, the second part having a proximal portion having a smaller radial dimension than the distal portion of the second part;
    a tubular body extending in the longitudinal direction, wherein the tubular body includes a first tubular part radially surrounding at least a portion of the first part and radially surrounding the second part; and
    a bonding agent filling between an outer periphery of at least the proximal portion of the second part of the shaft and an inner periphery of at least a proximal portion of the first tubular part of the tubular body;
    wherein the second part having an outer periphery, the outer periphery having a shape configured to increase a gap between the outer periphery and an inner periphery of at least the proximal portion of the first tubular part of the tubular body in a direction moving away from the first part.

2. The endoscope bonding structure according to claim 1, wherein
    the second part of the shaft is provided proximally relative to the first part of the shaft in the longitudinal direction, and
    the second outer diameter decreases gradually toward a proximal side of the second part of the shaft.

3. The endoscope bonding structure according to claim 1, wherein
    the second part of the shaft is provided proximally relative to the first part of the shaft in the longitudinal direction, and
    the second outer diameter decreases in a stepwise manner toward a proximal side of the second part of the shaft.

4. The endoscope bonding structure according to claim 1, wherein
    the tubular body includes a second part provided proximally relative to the first tubular part of the tubular body,
    the second part of the tubular body includes a ring that is freely movable on the inner periphery of the tubular body in the longitudinal direction, and
    the ring is biased to a distal side of the tubular body in the longitudinal direction by a spring.

5. The endoscope bonding structure according to claim 1, further comprising a blockage body covering an opening of the tubular body, the blockage body is disposed distally relative to the first part of the shaft.

6. The endoscope bonding structure according to claim 5, wherein the bonding agent is disposed between a distal end of the tubular body and a proximal end of the blockage body.

7. The endoscope bonding structure according to claim 1, wherein the tubular body includes a second tubular part provided proximally relative to the first tubular part of the tubular body, an inner diameter of the second tubular part of the tubular body is smaller than an inner diameter of the first tubular part of the tubular body.

8. The endoscope bonding structure according to claim 7, wherein a proximal end of the shaft is provided proximally relative to a distal end of the second tubular part of the tubular body.

9. The endoscope bonding structure according to claim 7, wherein a smallest diameter of the proximal portion of the second part of the shaft is larger than an inner diameter of the second tubular part of the tubular body.

10. The endoscope bonding structure according to claim 1, wherein an inner diameter of the first tubular part of the tubular body is greater than the first outer diameter of the first part of the shaft.

11. The endoscope bonding structure according to claim 1, wherein the second part of the shaft has a first length in the longitudinal direction, the first tubular part of the tubular body has a second length in the longitudinal direction, and the second length is equal to or longer than the first length.

12. The endoscope bonding structure according to claim 1, wherein the second outer diameter of the distal portion of the second part is a maximum second outer diameter.

13. The endoscope bonding structure according to claim 1, wherein the smaller radial dimension of the proximal portion of the second part comprises one or more longitudinal extending grooves.

14. The endoscope bonding structure according to claim 1, wherein
    the one or more longitudinal extending grooves comprises two or more longitudinal extending grooves, and
    the endoscope bonding structure further comprising a circumferential groove connecting the two or more longitudinal extending grooves.

15. The endoscope bonding structure according to claim 1, wherein the bonding agent is disposed continuously to fill a first space between the first and second parts and the inner periphery of the first tubular part and to fill a second space formed between a proximal face of the blocking body and a distal face of the tubular body.

16. An endoscope comprising:
    a distal end body extending in a longitudinal direction, wherein the distal end body comprises:
        a first part having a first outer diameter; and
        a second part having a distal portion having a second outer diameter smaller than the first outer diameter, the second part having a proximal portion having a smaller radial dimension than the distal portion of the second part;
    a tubular body extending in the longitudinal direction, wherein the tubular body includes a first tubular part radially surrounding at least a portion of the first part and radially surrounding the second part; and
    a bonding agent filling between the outer periphery of at least the proximal portion of the second part of the distal end body and an inner periphery of the tubular body;
    wherein the second part having an outer periphery, the outer periphery having a shape configured to increase a gap between the outer periphery and an inner periphery of at least the proximal portion of the first tubular part of the tubular body in a direction moving away from the first part.

17. The endoscope according to claim 16, wherein the tubular body includes a second tubular part provided proximally relative to the first tubular part of the tubular body, an inner diameter of the second tubular part of the tubular body is smaller than an inner diameter of the first tubular part of the tubular body.

18. The endoscope according to claim 16, wherein an inner diameter of the first tubular part of the tubular body is larger than the first outer diameter of the first part of the distal end body.

19. The endoscope according to claim 16, wherein the second part of the distal end body has a first length in the longitudinal direction, the first tubular part of the tubular body has a second length in the longitudinal direction, and the second length is equal to or longer than the first length.

* * * * *